United States Patent
Prewett et al.

(10) Patent No.: US 11,129,927 B2
(45) Date of Patent: *Sep. 28, 2021

(54) METHOD FOR FORMING HYDROGELS AND MATERIALS THEREFOR

(71) Applicant: Endologix LLC, Irvine, CA (US)

(72) Inventors: Donovan Prewett, Irvine, CA (US);
Paolo Mendoza, Tustin, CA (US);
Charles Bankert, Oceanside, CA (US);
Mehdi Durali, Carlsbad, CA (US)

(73) Assignee: Endologix LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/509,375

(22) Filed: Jul. 11, 2019

(65) Prior Publication Data

US 2019/0336655 A1 Nov. 7, 2019

Related U.S. Application Data

(63) Continuation of application No. 15/256,462, filed on Sep. 2, 2016, now Pat. No. 10,350,331, which is a (Continued)

(51) Int. Cl.
*A61L 31/06* (2006.01)
*A61L 31/14* (2006.01)
(Continued)

(52) U.S. Cl.
CPC .............. *A61L 31/145* (2013.01); *A61L 31/06* (2013.01); *A61L 31/18* (2013.01); *C08G 65/00* (2013.01);
(Continued)

(58) Field of Classification Search
None
See application file for complete search history.

(56) References Cited

U.S. PATENT DOCUMENTS

| 670,303 A | 3/1901 | Ashton |
| 5,330,528 A * | 7/1994 | Lazim ..................... A61F 2/07 606/194 |

(Continued)

FOREIGN PATENT DOCUMENTS

| CN | 1784430 A | 6/2006 |
| EP | 3 113 722 A1 | 1/2017 |

(Continued)

OTHER PUBLICATIONS

Notice on Reexamination dated Jun. 5, 2020, from application No. 201580012599.3.

(Continued)

*Primary Examiner* — Peter A Salamon
(74) *Attorney, Agent, or Firm* — Foley & Lardner LLP

(57) ABSTRACT

The present invention provides a dry powder that is suitable for use in forming a hydrogel and characterized by a stable composition at ambient conditions. The dry powder includes a prepolymer including a straight chain polyethylene glycol, and a thermally activated free radical initiator selected from the group consisting of sodium persulfate, potassium persulfate, and ammonium persulfate. The present invention also provides a method of forming the dry powder, and a method of preparing a hydrogel where a reaction mixture is formed including the dry powder and a buffered aqueous solution.

13 Claims, 1 Drawing Sheet

Related U.S. Application Data continuation of application No. PCT/US2015/019251, filed on Mar. 6, 2015.

(60) Provisional application No. 61/949,869, filed on Mar. 7, 2014.

(51) Int. Cl.
*G06Q 20/32* (2012.01)
*G06Q 20/40* (2012.01)
*A61L 31/18* (2006.01)
*C08G 65/00* (2006.01)

(52) U.S. Cl.
CPC ....... *G06Q 20/325* (2013.01); *G06Q 20/4016* (2013.01); *A61L 2300/44* (2013.01); *A61L 2400/06* (2013.01); *A61L 2430/20* (2013.01)

(56) References Cited

U.S. PATENT DOCUMENTS

| | | | | |
|---|---|---|---|---|
| 5,334,024 | A * | 8/1994 | Niznick | A61C 8/0001 433/172 |
| 5,643,464 | A * | 7/1997 | Rhee | A61K 47/60 522/1 |
| 6,312,462 | B1 * | 11/2001 | McDermott | A61F 2/07 623/1.25 |
| 6,703,037 | B1 * | 3/2004 | Hubbell | A61K 9/1635 424/426 |
| 6,818,018 | B1 | 11/2004 | Sawhney | |
| 6,964,667 | B2 * | 11/2005 | Shaolian | A61B 17/1671 606/195 |
| 7,001,431 | B2 * | 2/2006 | Bao | A61B 17/7097 606/247 |
| 7,057,019 | B2 * | 6/2006 | Pathak | C07K 14/745 530/362 |
| 7,872,068 | B2 * | 1/2011 | Khosravi | A61L 24/046 524/560 |
| 7,914,541 | B2 | 3/2011 | Sawhney et al. | |
| 8,591,950 | B2 | 11/2013 | Bennett et al. | |
| 10,350,331 | B2 * | 7/2019 | Prewett | G06Q 20/4016 |
| 2004/0002456 | A1 * | 1/2004 | Pathak | G06K 7/10831 530/362 |
| 2004/0105778 | A1 * | 6/2004 | Lee | A61K 9/145 422/22 |
| 2004/0204755 | A1 * | 10/2004 | Robin | A61F 2/07 623/1.21 |
| 2005/0079147 | A1 | 4/2005 | Delaey et al. | |
| 2006/0025853 | A1 * | 2/2006 | Evans | A61F 2/07 623/1.21 |
| 2007/0225427 | A1 | 9/2007 | Wright et al. | |
| 2007/0282366 | A1 * | 12/2007 | Khosravi | A61L 24/046 606/192 |
| 2008/0241267 | A1 * | 10/2008 | Verrijk | A61K 9/1694 424/499 |
| 2011/0104052 | A1 * | 5/2011 | Barnett | A61K 9/1617 424/1.21 |
| 2011/0293699 | A1 | 12/2011 | Bennett et al. | |
| 2016/0367731 | A1 * | 12/2016 | Prewett | A61L 31/06 |

FOREIGN PATENT DOCUMENTS

| | | |
|---|---|---|
| JP | 2004-359943 A | 12/2004 |
| JP | 2009-538695 | 11/2009 |
| JP | 6645979 B2 | 2/2020 |
| WO | WO-98/12274 A1 | 3/1998 |
| WO | WO-2004/099265 A1 | 11/2004 |
| WO | WO-2007/142916 A2 | 12/2007 |
| WO | WO-2015/134906 A1 | 9/2015 |

OTHER PUBLICATIONS

European Office Action dated Dec. 18, 2019, from application No. 15758921.9.
Japanese Office Action dated Mar. 23, 2021, from application No. 2019-194316.
Aldrich, Product Specification Poly(ethylene glycol) diacrylate, average Mn 10,000, dated Jun. 7, 2018, 1 page (Year: 2018).
Chinese Office Action dated Dec. 20, 2018, from application No. 201580012599.3.
Chinese Office Action dated May 13, 2019, from application No. 201580012599.3.
Chinese Office Action dated May 31, 2018 from Application No. 201580012599.3.
Chinese Office Action dated Sep. 26, 2017, from application No. 201580012599.3.
Extended European Search Report dated Nov. 7, 2017, from application No. 15758921.9.
Final Office Action dated Dec. 13, 2018, from U.S. Appl. No. 15/256,462.
Japanese Decision of Final Rejection dated Jun. 25, 2019, from application No. 2016-555580.
Japanese Office Action dated Oct. 30, 2018, from application No. 2016-555580.
Non-Final Office Action dated Jun. 13, 2018, from U.S. Appl. No. 15/256,462.
Notice of Allowance dated Mar. 11, 2019, from U.S. Appl. No. 15/256,462.
PCT/US2015/019251, "International Search Report and Written Opinion", dated Jun. 3, 2015, 13 pages.
Japanese Office Action dated Sep. 15, 2020, from application No. 2019-194316.

\* cited by examiner

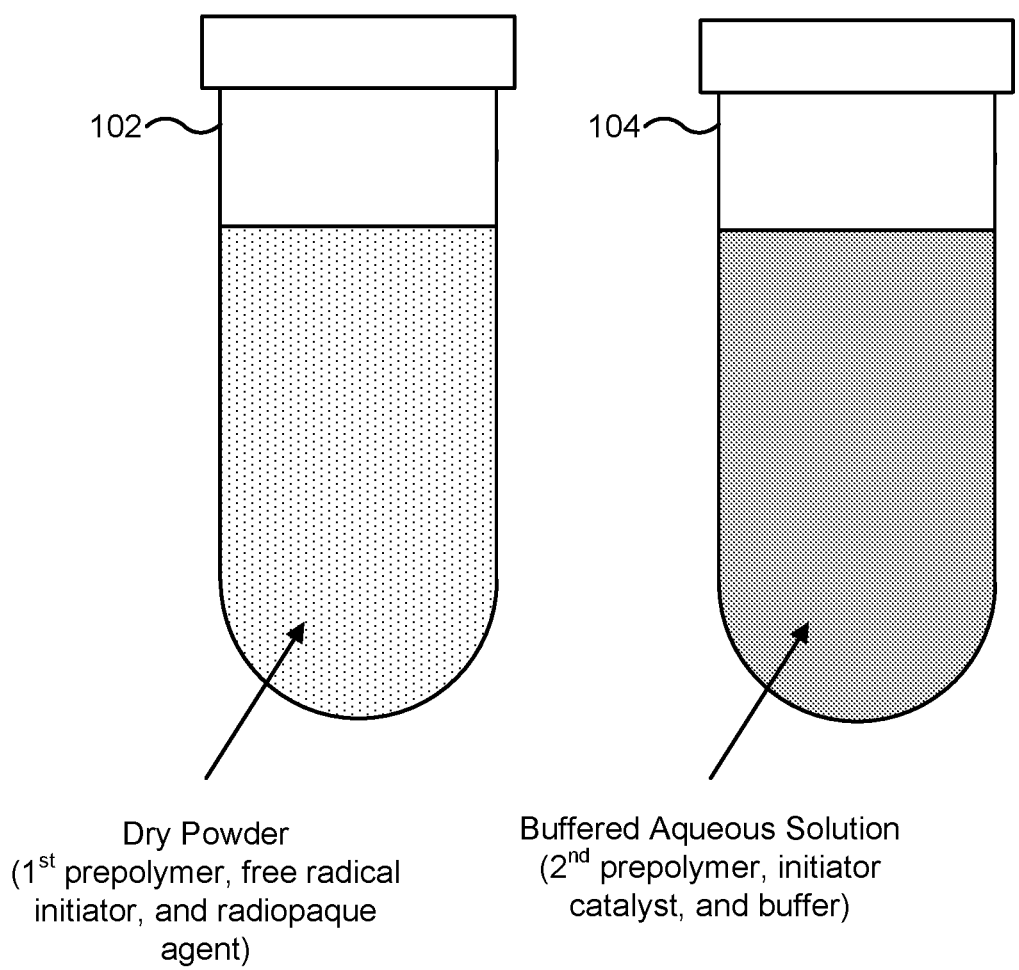

METHOD FOR FORMING HYDROGELS AND MATERIALS THEREFOR

CROSS-REFERENCES TO RELATED APPLICATIONS

The present application is a continuation of U.S. application Ser. No. 15/256,462, filed Sep. 2, 2016, which is a continuation of International Application No. PCT/US2015/019251, filed Mar. 6, 2015, which claims benefit and priority under 35 U.S.C. § 119(e) to U.S. Provisional Application No. 61/949,869, filed Mar. 7, 2014, incorporated in their entirety herein for all purposes.

BACKGROUND OF THE INVENTION

Aortic Aneurysms (AAA) and Thoracic Aortic Aneurysms (TAA) are weakened areas in the aorta that form balloon-like bulges, or sacs, in approximately the abdominal area. As blood flows through the aorta, the pressure of the blood pushes against the weakened wall, causing it to enlarge and often rupture. Ruptured AAA is a major cause of death in the United States.

In the past, clips and open surgery were the traditional interventional treatments for AAA and TAA. More recently, endografts, sometimes with stents for added stability, have been placed across the aneurysm to reduce the pressure on the aneurysm wall and prevent its enlargement and rupture.

Most recently, systems have been described where an expandable member of a device is introduced into the aneurysmal sac by means of minimally invasive surgical (MIS) techniques, e.g., guidance through the vasculature of a human patient using a guidewire. Flowable precursor materials are introduced into the expandable member, and the precursor materials undergo a chemical reaction, thereby causing the expandable member to expand and conform to the shape of the aneurysmal sac. As the materials harden, they lock the expandable member in place in the patient and stabilize the aneurysm. See, for example, U.S. Pat. Nos. 7,872,068 and 8,044,137, and U.S. Publication No. 2006/0222596, the contents of which are hereby incorporated by reference herein in their entirety. The expandable member may be, for example, a single-walled or double-walled balloon or endobag, or an inflatable cuff. Other examples of devices having an inflatable or expandable member are provided, for example, in International Publication No. WO 00/51522, U.S. Pat. Nos. 5,334,024, 5,330,528, 6,312,462, 6,964,667, and 7,001,431, and U.S. Publication Nos. 2004/0204755 and 2006/0025853, the contents of which are hereby incorporated by reference herein in their entirety.

The flowable precursor materials are typically polymer precursors which polymerize and cross-link to form hydrogels. One preferred type of polymer precursor is a material that can be polymerized by free radical polymerization. Typically this involves the polymerization/cross-linking of two prepolymers, each having terminal reactive groups that are susceptible to free radical polymerization, such as acrylates. The polymerization is effected by combining both prepolymers with a thermally activated low temperature free radical initiator and an initiator catalyst at physiological temperature.

To avoid unintended polymerization, i.e. prior to mixing all the components and allowing them to polymerize in situ in the expandable device, the components are typically stored in two separate aqueous solutions, one solution comprising one polymer precursor and the free radical initiator, and the other solution comprising the other polymer precursor and the initiator catalyst. In this way, the two polymer precursors are kept apart, as are the free radical initiator and the initiator catalyst.

In practice, the two solutions are delivered simultaneously or nearly simultaneously and then mixed, either ex vivo in a manifold, or in the expandable device itself. Because of the instability of thermally activated low temperature free radical initiators, the solution containing the free radical initiator must necessarily be kept frozen, i.e. at zero degrees Celsius or lower, until needed. Even so, the useful shelf life of the device or kit comprising such solutions is only 12 to 18 months.

The necessity that at least one solution be kept frozen is a serious practical disadvantage, inasmuch as the solution cannot easily be thawed and be ready for use as soon as a patient presents with an AAA that needs immediate treatment, particularly since rapid thawing by conventional techniques using large temperature differentials, e.g., hot water or microwave defrosting, cannot be used because of the thermal activation of the initiator.

What is needed is a material suitable for use in forming a hydrogel and characterized by a stable composition at ambient conditions, a method of making the material, and a method of preparing a hydrogel using the material. Surprisingly, the present invention meets this and other needs.

SUMMARY OF THE INVENTION

In one embodiment, the present invention provides a dry powder. The dry powder includes a prepolymer comprising a straight chain polyethylene glycol, and a thermally activated free radical initiator selected from the group consisting of sodium persulfate, potassium persulfate, and ammonium persulfate.

In another embodiment, the present invention provides a method of preparing a hydrogel. The method includes forming a reaction mixture comprising a dry powder and a buffered aqueous solution under conditions suitable to form the hydrogel. The dry powder includes a first prepolymer comprising a straight chain polyethylene glycol, and a thermally activated free radical initiator selected from the group consisting of sodium persulfate, potassium persulfate, and ammonium persulfate. The buffered aqueous solution includes a second prepolymer comprising a branched chain oligomeric polyethylene glycol, and an initiator catalyst selected from the group consisting of triethanolamine and tetramethylethylenediamine.

In another embodiment, the present invention provides a method of preparing a dry powder. The method includes preparing a solution. The solution includes a prepolymer comprising a straight chain polyethylene glycol, and a thermally activated free radical initiator selected from the group consisting of sodium persulfate, potassium persulfate, and ammonium persulfate. The solution is dehydrated to form the dry powder.

BRIEF DESCRIPTION OF THE DRAWINGS

FIG. 1 shows a simplified diagram of a kit including two cartridges individually containing a dry powder and a buffered aqueous solution suitable for forming a hydrogel.

DETAILED DESCRIPTION OF THE INVENTION

I. General

Embodiments described herein provide a dry powder suitable for use in forming a hydrogel and characterized by a stable composition at ambient conditions. The dry powder can include a prepolymer and a thermally activated free radical initiator, and can be characterized by a particle size of about 500 microns or less. The prepolymer can include a straight chain polyethylene glycol terminally derivatized with, for example, two acrylate groups, and characterized by a molecular weight of about 1 to 100 kiloDaltons. The thermally activated free radical initiator can be sodium persulfate, potassium persulfate, ammonium persulfate, or other suitable thermally activated free radical initiator. The dry powder can further include a radiopaque agent. Because of its stable composition, the dry powder can have a very long shelf life of more than 24 hours, more than 1 month, more than 1 year, more than 2 years, more than 3 years. In other embodiments, the dry powder may not degrade or may remain reactive for at least 1 year in an ambient environment or any non-frozen state.

The various embodiments also provide a method of preparing a hydrogel. The method includes forming a reaction mixture comprising a dry powder and a buffered aqueous solution under conditions suitable to form the hydrogel. The dry powder can include a first prepolymer and a thermally activated free radical initiator, and can be characterized by a particle size of about 500 microns or less. The first prepolymer can include a straight chain polyethylene glycol terminally derivatized, for example, with reactive group acrylates, diacrylates, triacrylates, methacrylates, dimethacrylates, trimethacrylates, or vinyl groups, and characterized by a molecular weight of about 1 to 100 kiloDaltons. The thermally activated free radical initiator can be aromatic amines, aliphatic amines, ferrous (iron) compounds, sodium persulfate, potassium persulfate, ammonium persulfate, or other suitable thermally activated free radical initiator. The buffered aqueous solution can include a second reactive component to make the cross-linked polymer, and an initiator catalyst. For example, the second reactive component can include a second prepolymer. The second prepolymer or a reactive component can include a branched chain oligomeric polyethylene glycol terminally derivatized with, for example, one or more acrylate, methacrylate, dimethacrylate, or vinyl groups, and can be characterized by a molecular weight of about 500 Daltons to about 2 kiloDaltons. The initiator catalyst can be any aromatic amine, aliphatic amine, or ferrous (iron) compound. In various embodiments, the initiator catalyst can be triethanolamine or N-alkyl substituted ethylenediamine derivatives including tetramethylethylenediamine. The buffered aqueous solution can further include a buffer that can be any suitable acid or base including but not limited to, sodium phosphate dibasic, sodium phosphate monobasic, sodium hydroxide, and hydrochloric acid. As a result of the fine particle size of the dry powder, dissolution can occur very rapidly (e.g., within 30 seconds or less) when the dry powder is introduced into the buffered aqueous solution (or reconstituted prior to mixing with the buffered aqueous solution).

Various embodiments also provide a method of preparing a dry powder. The method can include preparing a solution comprising a prepolymer and a thermally activated free radical initiator. The prepolymer can include a straight chain polyethylene glycol terminally derivatized with, for example, two acrylate groups, and characterized by a molecular weight of about 1 to 100 kiloDaltons. The thermally activated free radical initiator can be sodium persulfate, potassium persulfate, ammonium persulfate, or other suitable thermally activated free radical initiator. The method can further include dehydrating the solution to form the dry powder. Dehydrating can include lyophilizing, spray drying, or other suitable process for removing water from the solution. The dry powder can be characterized by a particle size of about 500 microns or less. In various embodiments, the dry powder may include various compounds that are of different particle sizes. In various embodiments, the largest particle size may be 500 microns, 400 microns, 200 microns, or 100 microns. In other embodiments, some particles may be larger than 500 microns but the concentration of particles that are larger can be less than 10%, less than 5%, or less than 2% of the total number of particles in the dry powder.

As described above, previous methods for treating AAA have included forming a material in situ by increasing the volume of an expandable member of a medical device. The expandable member when expanded by flowable material conforms to the shape of the aneurysm in which it is contained, and once allowed to harden, fixes the medical device in place. The material is formed by the free radical polymerization of two polymer precursors in an aqueous solution in the presence of a thermally activated free radical initiator and an initiator catalyst. The polymerization is carried out, for example, inside an endograft comprising a single-walled or double-walled balloon or endobag.

In various processes, two solutions are in separate containers, for example, syringes, with each container communicating with a tube. One solution comprises a first prepolymer and either the free radical initiator or the initiator catalyst, and the other solution comprises a second prepolymer and the other of the initiator and the catalyst. The solutions are delivered under pressure through the tubes to a manifold where they are mixed. The manifold may comprise various structures to ensure thorough mixing. The resulting solution is then delivered via another tube to the expandable member where polymerization occurs, the expandable member expanding to conform to the shape of a surrounding aneurysm, and time passes to allow the polymerization to progress. Once solution delivery is concluded, the tube is withdrawn from the expandable member allowing the polymerizing mixture to be sealed within the expandable member. The medical device comprising the expandable member is typically delivered to the site of the aneurysm in the patient by means of a catheter that is put into place over a guidewire. Alternatively, no manifold is used and the two solutions are instead mixed in the expandable member.

The presence of the free radical initiator together with a prepolymer in one of the solutions being introduced is problematic in that it necessitates that this solution be kept frozen, and thawed only immediately before use in the operating theatre. Thawing by traditional means involving large temperature differentials such as hot water or microwave treatment is not possible due to the thermal activation of the initiator. Moreover, even at ambient temperature the initiator in solution is unstable and can result in degradation of the polymer precursor, such as by premature polymerization, thereby resulting in an unacceptable shelf life.

In embodiments of the present invention, the thermally activated free radical initiator and one of the prepolymers can be provided in the form of a dry powder characterized by a stable composition and a rapid dissolution rate when reconstituted with water or introduced into an aqueous solution comprising the other reactive components and initiator catalyst. As a result, the powdered prepolymer and free radical initiator need not be stored at freezer temperature (e.g., −20° C.), overall shelf life is improved, and prep time prior to surgery is reduced due to the dry powder dissolving in less time than that required to completely thaw the solution in a frozen state. Additionally the dry powder formulation and separate buffer components provide the use of terminal sterilization methods. These methods, which may include e-beam and gamma irradiation for the dry powder and steam sterilization for the liquid component, are not suitable for use with the prior art process. Terminal sterilization eliminates the need to continually validate aseptic processing. Moreover, such advantages are provided without sacrificing the desirable mechanical properties associated with hydrogels formed by way of existing processes.

II. Definitions

"Hydrogel" refers to a highly-interdependent, biphasic matrix consisting of a solid component (usually a polymer, and more commonly a highly cross-linked polymer) that has both hydrophilic and hydrophobic character. Additionally, the matrix has a liquid component (e.g., water) that is retained in the matrix by intermolecular forces. The hydrophobic character provides the matrix with a degree of water insolubility while the hydrophilic character affords water permeability.

"Dry powder" refers to a solid substance substantially free of water and in the form of fine particles.

"Prepolymer" refers to a polymer precursor in the form of a monomer or system of monomers in an intermediate molecular mass state, and that is capable of further polymerization by one or more reactive groups to form a higher molecular mass or cross-linked state. Prepolymers can include polyethylene glycol among other compounds. Prepolymers can be terminally derivatized with one or more active groups. Active groups useful in the present invention include acrylate or vinyl groups. Exemplary acrylate groups include, but are not limited to, diacrylates, triacrylates, methacrylates, dimethacrylates, trimethacrylates, and the like.

"Thermally activated free radical initiator" refers to a substance that promotes radical reactions above a particular temperature. Radical reactions useful in the present invention can include polymerization reactions where prepolymers are cross-linked to form a hydrogel. Thermally activated free radical initiators can include persulfates. Exemplary persulfates include, but are not limited to, sodium persulfate, potassium persulfate, ammonium persulfate, and the like.

"Buffered aqueous solution" refers to an aqueous solution comprising a mixture of a weak acid and its conjugate base, or vice versa, such that an equilibrium between the acid and conjugate base is present that resists changes in pH when a strong acid or base is added to the solution. Buffers useful in the present invention can include any suitable pH stabilizing salts. Exemplary buffers include, but are not limited to, phosphate, sodium phosphate dibasic, sodium phosphate monobasic, hydrochloric acid, sodium hydroxide, sodium hypophosphate, and the like.

"Initiator catalyst" refers to a substance that increases the rate of a chemical reaction. Chemical reactions useful in the present invention can include radical reactions, such as a polymerization reaction where prepolymers are cross-linked to form a hydrogel. Exemplary initiator catalysts include, but are not limited to, triethanolamine, tetramethylethylenediamine, aromatic amines, aliphatic amines, ferrous (iron) compounds, and the like.

"Radiopaque agent" refers to a substance that improves the visibility of internal bodily structures in X-ray based imaging techniques. Radiopaque agents useful in the present invention include, but are not limited to, compounds that may include iodine or the like. Exemplary radiopaque agents can include diatrizoate, metrizoate, ioxaglate, iopamidol, iohexol, loxilan, iopromide, iodixanol, and the like. Such radiopaque agents comprising iodine can further comprise sodium including, but not limited to, sodium diatrizoate.

"Stable composition at ambient conditions" refers to a composition that does not begin to decompose at standard ambient temperature and pressure (SATP) which refers to a temperature of about 25° C. and an absolute pressure of about 0.987 atm. In various embodiments stable may include beginning to slowly decompose such that the material remains reactive for longer than about 48 hours to 1 year to effectively form a cross-linked polymer in less than 5 minutes.

"Physiological temperature" refers to the body temperature of a patient which is typically about 37° C.

"Lyophilization" refers to a dehydration process where a material is frozen and then the surrounding pressure reduced to allow frozen water in the material to sublimate from the solid to gas phase, thereby forming a dry powder.

"Spray drying" refers to a dehydration process where a dry powder is formed from a liquid or slurry that is dried rapidly using a gas (e.g., may be heated) such as air or nitrogen.

"Dry blending" refers to a process where dry powders are mechanically mixed to form a homogenous dry powder mixture.

III. Dry Powders

Embodiments include providing a dry powder suitable for use in forming a hydrogel and characterized by a stable composition at ambient conditions. Various embodiments provide a dry powder including a prepolymer comprising a straight chain polyethylene glycol, and a thermally activated free radical initiator that can be sodium persulfate, potassium persulfate, ammonium persulfate, organic peroxides, or vinyl groups.

The dry powder can be characterized by any suitable particle size. In some embodiments, the dry powder can be characterized by a particle size of about 5 mm or less, 4 mm or less, 3 mm or less, 1 mm or less, 900 microns or less, 800 microns or less, 700 microns or less, or about 600 microns or less. In some embodiments, the dry powder can be characterized by a particle size of about 500 microns or less.

The dry powder can be formed using any suitable dehydration or compounding processes. In some embodiments, the dry powder can be a lyophilized powder, a dry blended powder, or a spray dried powder. In some embodiments, the dry powder can be a lyophilized powder.

The straight chain polyethylene glycol can be terminally derivatized with one or more active groups. In some embodiments, the straight chain polyethylene glycol can be terminally functionalized with reactive groups. Suitable reactive groups can include, but are not limited to, acrylates, diacrylates, triacrylates, methacrylates, dimeathacrylates, vinyl groups, and the like.

The prepolymer can be characterized by any suitable molecular weight. In some embodiments, the prepolymer can be characterized by a molecular weight of about 1 to 100 kiloDaltons. In some embodiments, the prepolymer can be characterized by a molecular weight of about 4 to 90 kiloDaltons, 8 to 80 kiloDaltons, 12 to 70 kiloDaltons, 16 to 60 kiloDaltons, or about 20 to 50 kiloDaltons. In some embodiments, the prepolymer can be characterized by a molecular weight of about 25, 28, 30, 32, 35, 37, 40, 42, or 45 kiloDaltons.

In some embodiments, the dry powder can further include any suitable buffer comprising pH stabilizing salts. Suitable buffers include, but are not limited to, phosphate, sodium phosphate dibasic, sodium phosphate monobasic, hydrochloric acid, sodium hydroxide, sodium hypophosphate, and the like. In some embodiments, the dry powder can include a buffer that can be phosphate, sodium phosphate dibasic, or sodium phosphate monobasic.

In some embodiments, the dry powder can further include a radiopaque agent. Any suitable radiopaque agent that improves the visibility of internal body structures (e.g., an aorta) in X-ray imaging techniques can be used. Suitable radiopaque agents include, but are not limited to, compounds comprising iodine such as diatrizoate, metrizoate, ioxaglate, iopamidol, iohexol, loxilan, iopromide, iodixanol, and the like. Such suitable radiopaque agents comprising iodine can further comprise sodium. For example, in some embodiments, the dry powder can include a sodium diatrizoate radiopaque agent.

In some embodiments, the dry powder can be a lyophilized powder including the prepolymer comprising the straight chain polyethylene glycol, wherein the straight chain polyethylene glycol can be terminally derivatized with two acrylate groups, and wherein the prepolymer can be characterized by a molecular weight of about 1 to 100 kiloDaltons. The dry powder can further include the thermally activated free radical initiator that can be sodium persulfate, potassium persulfate, or ammonium persulfate, a phosphate buffer, and a sodium diatrizoate radiopaque agent. The dry powder can be characterized by a particle size of about 500 microns or less, wherein the dry powder is further characterized by a stable composition at ambient conditions.

IV. Methods of Preparing Hydrogel Using Dry Powder

Various embodiments include a method of making a hydrogel using a dry powder characterized by a stable composition at ambient conditions. In some embodiments, the method includes forming a reaction mixture comprising a dry powder and a buffered aqueous solution under conditions suitable to form the hydrogel. The dry powder can include a first prepolymer comprising a straight chain polyethylene glycol, and a thermally activated free radical initiator that can be sodium persulfate, potassium persulfate, or ammonium persulfate. The buffered aqueous solution can include a second prepolymer comprising a branched chain oligomeric polyethylene glycol, and an initiator catalyst that can be triethanolamine or tetramethylethylenediamine.

The dry powder can be characterized by any suitable particle size. In some embodiments, the dry powder can be characterized by a particle size of about 5 mm or less, 4 mm or less, 3 mm or less, 1 mm or less, 900 microns or less, 800 microns or less, 700 microns or less, or about 600 microns or less. In some embodiments, the dry powder can be characterized by a particle size of about 500 microns or less.

The dry powder can be formed using any suitable dehydration or compounding processes. In some embodiments, the dry powder can be a lyophilized powder, a dry blended powder, or a spray dried powder. In some embodiments, the dry powder can be a lyophilized powder.

The straight chain polyethylene glycol and the branched chain oligomeric polyethylene glycol can each be terminally derivatized with one or more active groups. In some embodiments, the straight chain polyethylene glycol can be terminally derivatized with two acrylate groups, and the branched chain oligomeric polyethylene glycol can be terminally derivatized with three acrylate groups. Suitable acrylate groups include, but are not limited to, diacrylates, triacrylates, methacrylates, dimethylcrylates, and the like.

The first prepolymer and the second prepolymer or a reactive component can each be characterized by any suitable molecular weight. In some embodiments, the first prepolymer can be characterized by a molecular weight of about 1 to 100 kiloDaltons, and the second prepolymer can be characterized by a molecular weight of about 500 Daltons to about 2 kiloDaltons. In some embodiments, the first prepolymer can be characterized by a molecular weight of about 4 to 90 kiloDaltons, 8 to 80 kiloDaltons, 12 to 70 kiloDaltons, 16 to 60 kiloDaltons, or about 20 to 50 kiloDaltons. In some embodiments, the first prepolymer can be characterized by a molecular weight of about 25, 28, 30, 32, 35, 37, 40, 42, or 45 kiloDaltons. In some embodiments, the second prepolymer can be characterized by a molecular weight of about 575 Daltons to about 1.8 kiloDaltons, 650 Daltons to about 1.6 kiloDaltons, 725 Daltons to about 1.4 kiloDaltons, or about 800 Daltons to about 1.2 kiloDaltons. In some embodiments, the second prepolymer or reactive component can be characterized by a molecular weight of about 1.0, 1.1, 1.2, 1.3, 1.4, 1.5, or 1.6 kiloDalton.

In some embodiments, at least one of the dry powder and the buffered aqueous solution can further include any suitable buffer comprising pH stabilizing salts. Suitable buffers include, but are not limited to, phosphate, sodium phosphate dibasic, sodium phosphate monobasic, hydrochloric acid, sodium hydroxide, sodium hypophosphate, and the like. In some embodiments, at least one of the dry powder and the buffered aqueous solution can include a buffer that can be phosphate, sodium phosphate dibasic, or sodium phosphate monobasic.

In some embodiments, at least one of the dry powder and the buffered aqueous solution can further include a radiopaque agent. Any suitable radiopaque agent that improves the visibility of internal body structures (e.g., an aorta) in X-ray imaging techniques can be used. Suitable radiopaque agents include, but are not limited to, compounds comprising iodine such as diatrizoate, sodium diatrizoate, metrizoate, ioxaglate, iopamidol, iohexol, loxilan, iopromide, iodixanol, and the like. Such suitable radiopaque agents comprising iodine can further comprise sodium. For example, in some embodiments, at least one of the dry powder and the buffered aqueous solution can include a sodium diatrizoate radiopaque agent.

The reaction mixture can include any molar ratio of the second prepolymer to the first prepolymer suitable for forming the desired hydrogel. In some embodiments, the molar ratio of the second prepolymer to the first prepolymer in the reaction mixture can be about 200:1 to 1000:1. In some embodiments, the molar ratio of the second prepolymer to the first prepolymer in the reaction mixture can be about 225:1 to 900:1, 250:1 to 800:1, 275:1 to 700:1, 300:1 to 600:1, or about 325:1 to 500:1. In some embodiments, the molar ratio of the second prepolymer to the first prepolymer in the reaction mixture can be about 400:1.

Upon forming the reaction mixture, the dry powder can dissolve in the buffered aqueous solution over any suitable interval of time. In some embodiments, the dry powder can dissolve in the buffered aqueous solution over a time interval of about 1 minutes or less. In some embodiment, the dry powder can dissolve in the buffered solution over a time interval of about 45 seconds or less, or 30 second or less. In some embodiments, the dry powder can dissolve in the buffered aqueous solution over a time interval of about 28 seconds or less, 26 seconds or less, 24 seconds or less, 22 seconds or less, 20 seconds or less, 18 seconds or less, or about 16 seconds or less. In some embodiments, the dry powder can dissolve in the buffered aqueous solution over a time interval of about 15 seconds or less.

In some embodiments, the dry powder can dissolve in the buffered aqueous solution to form a flowable aqueous solution, and polymerization of the flowable aqueous solution can occur at a physiological temperature over a time interval of about 10 minutes or less. In some embodiments, polymerization of the flowable aqueous solution can occur at a physiological temperature over a time interval of about 9 minutes or less, 8 minutes or less, 7 minutes or less, 6 minutes or less, 5 minutes or less, 4 minutes or less, or about 3 minutes or less. In some embodiments, the flowable aqueous solution can be introduced into a medical device, and the polymerization of the flowable aqueous solution can occur within the medical device at the physiological temperature. For example, the flowable aqueous solution can be introduced through a fill tube into the internal volume of an expandable member of a medical device where, at physiological temperature, a polymerization cross-linking reaction is initiated to produce a hydrogel having the desired properties.

In some embodiments, the buffered aqueous solution can include sufficient water to compensate for any water removed during preparation of the dry powder (e.g., via lyophilization or spray-drying) and to ensure sufficiently low viscosity of the final aqueous solution so that it is flowable. In some other embodiments, the dry powder can be reconstituted with water prior to mixing with the buffered aqueous solution to form the reaction mixture. For example, instead of introducing the dry powder into the buffered aqueous solution (or vice versa), the dry powder can alternatively be reconstituted (e.g., with distilled water) and the reconstituted dry powder then mixed with the buffered aqueous solution to form the reaction mixture. The reconstituted dry powder and buffered aqueous solution can be mixed prior to introducing into a fill tube, or introduced into separate tubes and mixed in a mixing device, and then delivered through the fill tube into the internal volume of the expandable member.

In some embodiments, the dry powder and the buffered aqueous solution can be stored in cartridges provided individually or, alternatively, together in the form of a kit. FIG. 1 shows a simplified diagram of a kit 100. As shown in FIG. 1, kit 100 can include a first cartridge 102 containing the dry powder and a second cartridge 104 containing the buffered aqueous solution. As described herein, the dry powder contained in first cartridge 102 can include the first prepolymer, the thermally activated free radical initiator, and the radiopaque agent, and the buffered aqueous solution contained in second cartridge 104 can include the second prepolymer, the initiator catalyst, and the buffer. First cartridge 102 and second cartridge 104 can each include a rubber seal so that water or an aqueous solution may be added and withdrawn. In some embodiments, kit 100 can include additional components such as a dispensing device (e.g., a syringe) for dispensing a flowable aqueous solution, a catheter having a lumen, a fill tube disposed within the lumen, and the medical device (e.g., an endograft) comprising the expandable member (e.g., a endobag).

In some embodiments, the method of the present invention of preparing a hydrogel can include reconstituting the dry powder with water, wherein the dry powder can be a lyophilized powder characterized by a particle size of about 500 microns or less, and wherein the dry powder can include the first prepolymer comprising a straight chain polyethylene glycol. The straight chain polyethylene glycol can be terminally derivatized with two acrylate groups, wherein the first prepolymer can be characterized by a molecular weight of about 1 to 100 kiloDaltons. The dry powder can further include the thermally activated free radical initiator that can be sodium persulfate, potassium persulfate, or ammonium persulfate, a phosphate buffer, and a sodium diatrizoate radiopaque agent. The method can further include forming the reaction mixture under the conditions suitable to form the hydrogel, wherein the reaction mixture can comprise the reconstituted dry powder and the buffered aqueous solution. The buffered aqueous solution can include the second prepolymer comprising a branched chain oligomeric polyethylene glycol, wherein the branched chain oligomeric polyethylene glycol can be terminally derivatized with three acrylate groups, and wherein the second prepolymer can be characterized by a molecular weight of about 500 Daltons to about 2 kiloDaltons. The molar ratio of the second prepolymer to the first prepolymer in the reaction mixture can be about 200:1 to 1000:1. The buffered aqueous solution can further include the initiator catalyst that can be triethanolamine or tetramethylethylenediamine, and a phosphate buffer, wherein the dry powder can dissolve in the buffered aqueous solution to form a flowable aqueous solution over a time interval of about 30 second or less. The method can further include introducing the flowable aqueous solution into a medical device, wherein polymerization of the flowable aqueous solution can occur within the medical device at a physiological temperature over a time interval of about 10 minutes or less.

V. Methods of Preparing Dry Powder

Various embodiments provide a method of preparing a dry powder suitable for use in forming a hydrogel and characterized by a stable composition at ambient conditions. In some embodiments, the method includes preparing a solution. The solution can include a prepolymer comprising a straight chain polyethylene glycol, and a thermally activated free radical initiator that can be sodium persulfate, potassium persulfate, or ammonium persulfate. The method can further include dehydrating the solution to form the dry powder.

The dry powder can be characterized by any suitable particle size. In some embodiments, the dry powder can be characterized by a particle size of about 5 mm or less, 4 mm or less, 3 mm or less, 1 mm or less, 900 microns or less, 800 microns or less, 700 microns or less, or about 600 microns or less. In some embodiments, the dry powder can be characterized by a particle size of about 500 microns or less, 400 microns or less, or about 300 microns or less.

The straight chain polyethylene glycol can be terminally derivatized with one or more active groups, and the prepolymer can be characterized by any suitable molecular weight. In some embodiments, the straight chain polyethylene glycol can be terminally derivatized with two acrylate groups, and the prepolymer can be characterized by a molecular weight of about 1 to 100 kiloDaltons. Suitable acrylate groups include, but are not limited to, methacrylates, diacrylates, triacrylates, and the like. In some embodiments, the prepolymer can be characterized by a molecular weight of about 4 to 90 kiloDaltons, 8 to 80 kiloDaltons, 12 to 70 kiloDaltons, 16 to 60 kiloDaltons, or about 20 to 50 kiloDaltons. In some embodiments, the prepolymer can be characterized by a molecular weight of about 25, 28, 30, 32, 35, 37, 40, 42, or 45 kiloDaltons.

In some embodiments, the solution can further include any suitable buffer comprising pH stabilizing salts, and a radiopaque agent. Suitable buffers include, but are not limited to, phosphate, sodium phosphate dibasic, sodium phosphate monobasic, hydrochloric acid, sodium hydroxide, sodium hypophosphate, and the like. Suitable radiopaque agents include, but are not limited to, compounds comprising iodine such as diatrizoate, metrizoate, ioxaglate, iopamidol, iohexol, loxilan, iopromide, iodixanol, and the like. Such suitable radiopaque agents comprising iodine can further comprise sodium. For example, a suitable radiopaque agent can be sodium diatrizoate. In some embodiments, the solution can further include a buffer that can be phosphate, sodium phosphate dibasic, or sodium phosphate monobasic, and a radiopaque agent.

The solution can be filtered prior to dehydration using a filter characterized by any suitable pore size. In some embodiments, the solution can be filtered before dehydration using a filter characterized by a pore size of about 0.5, 0.4, 0.3, 0.2, or 0.1 microns or less. In some embodiments, the solution can be filtered before dehydration using a filter characterized by a pore size of about 0.19 microns or less, 0.18 microns or less, 0.17 microns or less 0.16 microns or less, or about 0.15 microns or less. In various embodiments, the filter may be characterized by any pore size that enables sterile filtration.

The solution can be dehydrated using any suitable process that removes water from the solution leaving behind the dry powder. In some embodiments, dehydrating the solution can include lyophilizing or spray drying the solution or a combination of the two. Lyophilization can be performed by freezing the solution to a temperature of between about −20 and −50° C. and at a pressure of about 160 to 240 mTorr for at least about 12 hours. Spray drying can be performed by rapidly drying the solution using a hot gas such as air or nitrogen. A combination of spray drying and lyophilization could also be used by using a spray orifice to create controlled particle size droplets which are collected frozen then dried using lyophilization. Yet another method includes utilizing spray drying with low temperature gas to create small particles with minimal moisture and utilizing a secondary process such as vacuum drying to further reduce the powder moisture to acceptable levels (<1%).

In addition to forming a dry powder by dehydration processes such as lyophilization or spray drying, a dry blending process can be used where solid powders are mechanically mixed to form a homogeneous powder mixture. In some embodiments, solid powders of the prepolymer, the thermally activated free radical initiator, and the radiopaque agent can be dry blended to form a homogeneous powder mixture which can be isolated from water until the hydrogel is to be formed. To form the reaction mixture, the dry blended powder can be mixed with the buffered aqueous solution, or reconstituted with water with the reconstituted dry powder solution being mixed with the buffered aqueous solution.

Dissolution rates depend on the solid ingredient solubility and surface area as well as solid/liquid mixing efficiency. While solubility is an inherent property of chemicals, surface area can be manipulated by mechanical or physical means. Reducing particle size can significantly increase surface area (as they are inversely proportional to the second power) and as a result greatly enhance dissolution rate. This can be especially beneficial for hard to dissolve components such as potassium persulfate which is crystalline in nature (e.g., needle type crystals having a size of 1-3 mm). Accordingly, in some embodiments, the particle size of individual components can be controlled through processing techniques such as milling, grinding, spray drying, and the like.

In some embodiments, the prepolymer, thermally activated free radical initiator, and radiopaque agent can each be processed such that they are characterized by a particle size of about 500 microns or less, 100 microns or less, and 50 microns or less, respectively. When the desired particle size of each component is obtained, the individual powders can be mixed in the appropriate ratios using a dry blending process. The ratios of the dry blended powders can be adjusted such that, when mixed with a buffered aqueous solution including the cross-linking prepolymer and initiator catalyst at the proper stoichiometry, a radiopaque hydrogel is formed having the desired properties. In some embodiments, the weight percent of the prepolymer, free radical initiator, and radiopaque agent in the dry powder can be about 56-58%, 28-30%, and 14-16%, respectively.

In some embodiments, the dry powder can be characterized by a particle size of about 500 microns or less, and the method of the present invention of preparing the dry powder can include preparing the solution. The solution can include the prepolymer comprising a straight chain polyethylene glycol, wherein the straight chain polyethylene glycol can be terminally derivatized with two acrylate groups, and wherein the prepolymer can be characterized by a molecular weight of about 1 to 100 kiloDaltons. The solution can further include the thermally activated free radical initiator that can be sodium persulfate, potassium persulfate, or ammonium persulfate, a phosphate buffer, and a sodium diatrizoate radiopaque agent. The method can further include filtering the solution using a filter characterized by a pore size of about 0.5, 0.4, 0.3, 0.2, or 0.1 microns or less, and lyophilizing the solution to form the dry powder.

In various embodiments, upon preparing the solid prepolymer mixture, the solid prepolymer mixture may be stored for a period of time (e.g., 1 day, 3 days, 1 week, 1 month, 2 months, 3 months, 4 months, 7 months, or up to 1 year or more) prior to being shipped to a customer location. The solid prepolymer mixture may be dissolved into an aqueous solution with an activator at the customer location prior to the aqueous prepolymer being inserted via an endovascular device into a patient. In some embodiments, the solid prepolymer may contain some trace amounts of water or liquid, however, the small amounts of liquid does not degrade the majority of the prepolymer.

VI. Example

Example 1

Preparing a Dry Powder and a Hydrogel Therefrom

This example provides a method according to the present invention of preparing a dry powder, and also preparing a hydrogel using the dry powder.

A first solution (C1) was prepared from the following components based on a 1 liter batch size: (i) 40 grams of polyethylene glycol diacrylate having an average molecular weight of 35 kiloDaltons (PEG-D); (ii) 20 grams of sodium diatrizoate; (iii) 10.2 grams of potassium persulfate; and (iv) 940 grams of 0.02 M phosphate buffer solution having a pH of 8.0.

The C1 solution was filtered through a 0.2 micron filter and 20 mL was dispensed into a serum vial. The serum vial was placed in a tray lyophilizer and freeze dried at −40° C. and at a pressure of 200 mTorr for about 12-72 hours. Once all the water was removed with only a dry powder remaining, the vial was sealed with a rubber stopper.

A second solution (C2) was prepared from the following components based on a 1 liter batch size: (i) 535 grams of ethoxylated (20) trimethylolpropane triacrylate having an average molecular weight of 1.1 kilaDaltons (PEG-T); (ii) 9.4 grams of triethanolamine; and (iii) 540 grams of 0.02 M phosphate buffer solution having a pH of 8.0.

20 mL of the C2 solution was diluted with approximately 19 mL of water (i.e. the amount of water removed from the serum vial during lyophilization of the C1 solution) and placed in a syringe. A vented cap having a Luer Lock fitting was inserted through the rubber stopper of the serum vial. The syringe containing the diluted C2 solution was attached to the vented cap and the diluted C2 solution was dispensed into the serum vial. The lyophilized powdered C1 was dissolved within 1-2 seconds. The vial was then inverted and the mixed solution withdrawn into the syringe.

The syringe was attached to the proximal end of a lumen of a catheter, the distal end of which was connected to a polyurethane endobag. The endobag was placed in a 37° C. water bath. The mixed solution in the syringe was dispensed over about 20 seconds through the lumen of the catheter into the attached endobag. Polymerization was observed to be complete after about 7 minutes.

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A dry powder mixture comprising:
   a non-crosslinked prepolymer comprising a straight chain polyethylene glycol; and
   a thermally activated free radical initiator selected from the group consisting of sodium persulfate, potassium persulfate, and ammonium persulfate
   wherein the dry powder mixture is characterized by a particle size of about 500 microns or less, and
   wherein the dry power mixture is stable at ambient conditions.

2. The dry powder of claim 1;
   wherein the dry powder may be transported at ambient temperature from one location to another location for a period of time without degrading;
   wherein the dry powder may be mixed into a polymerizable solution; and
   wherein the dry powder is terminally sterilized.

3. The dry powder of claim 1, wherein the dry powder is selected from the group consisting of a lyophilized powder, dry blended powder, and spray dried powder.

4. The dry powder of claim 1, wherein the dry powder is a lyophilized powder.

5. The dry powder of claim 1, wherein the straight chain polyethylene glycol is terminally derivatized with acrylate, methacrylate, vinyl, or substituted vinyl end groups.

6. The dry powder of claim 1, wherein the prepolymer is characterized by a molecular weight of about 1 to 100 kiloDaltons.

7. The dry powder of claim 1, further comprising a buffer selected from the group consisting of phosphate, sodium phosphate dibasic, and sodium phosphate monobasic.

8. The dry powder of claim 1, further comprising a radiopaque agent.

9. The dry powder of claim 1, wherein the dry powder is a lyophilized powder comprising:
   the prepolymer comprising a straight chain polyethylene glycol, wherein the straight chain polyethylene glycol is terminally derivatized with two acrylate groups, and wherein the prepolymer is characterized by a molecular weight of about 1 to 100 kiloDaltons;
   the thermally activated free radical initiator selected from the group consisting of sodium persulfate, potassium persulfate, and ammonium persulfate;
   a phosphate buffer; and
   a sodium diatrizoate radiopaque agent, wherein the dry powder is characterized by a stable composition at ambient conditions.

10. A dry powder mixture comprising
    a first non-crosslinked prepolymer comprising a straight chain polyethylene glycol, wherein the straight chain polyethylene glycol is terminally derivatized with two acrylate groups; and
    a thermally activated free radical initiator selected from the group consisting of sodium persulfate, potassium persulfate, and ammonium persulfate;
    wherein the dry powder is characterized by a particle size of about 500 microns or less, wherein the dry powder is further characterized by a stable composition at ambient conditions,
    and wherein the dry powder forms a hydrogel under suitable conditions when combined with a buffered aqueous solution comprising:
    a second prepolymer comprising a branched chain oligomeric polyethylene glycol; and an initiator catalyst.

11. The dry powder of claim 10, further comprising a radiopaque agent.

12. The dry powder of claim 10, wherein the dry powder is lyophilized powder, dry blended powder or a spray dried powder.

13. A kit comprising:
    a first container comprising a dry powder mixture comprising a non-cross linked straight chain polyethylene glycol terminally derivatized with two acrylate groups, and a thermally activated free radical initiator comprising a persulfate, wherein the dry powder mixture is characterized by a particle size of about 500 microns or less, and
    wherein the dry power mixture is stable at ambient conditions;
    a second container comprising a branched chain oligomeric polyethylene glycol; and
    a third container comprising an initiator catalyst and a buffer;
    wherein the combination of the first, second and third container contents forms a hydrogel under suitable conditions.

* * * * *